United States Patent
Nuccio et al.

(10) Patent No.: US 10,392,627 B2
(45) Date of Patent: Aug. 27, 2019

(54) METHODS AND COMPOSITIONS FOR EXPRESSION CASSETTES COMPRISING A MAIZE GENE-DERIVED INTRON FOR ENHANCED EXPRESSION

(71) Applicant: Syngenta Participations AG, Basel (CH)

(72) Inventors: Michael L. Nuccio, Research Triangle Park, NC (US); Jonathan Cohn, Research Triangle Park, NC (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/375,439

(22) Filed: Dec. 12, 2016

(65) Prior Publication Data
US 2017/0175157 A1    Jun. 22, 2017

Related U.S. Application Data

(60) Provisional application No. 62/269,320, filed on Dec. 18, 2015.

(51) Int. Cl.
*C12N 15/82*    (2006.01)

(52) U.S. Cl.
CPC .................. *C12N 15/8216* (2013.01)

(58) Field of Classification Search
None
See application file for complete search history.

(56) References Cited

U.S. PATENT DOCUMENTS 5,304,712 A * 4/1994 Harper, II .................. A01H 5/10
435/412

OTHER PUBLICATIONS

Callis et al. Introns increase gene expression in cultured maize cells. (1987) Genes and Development; vol. 1; pp. 1183-1200) (Year: 1987).*
Fromm et al. Inheritance and expression of chimeric genes in the progeny of transgenic maize plants. (1990) Biotechnology; vol. 8; pp. 833-839 (Year: 1990).*

* cited by examiner

Primary Examiner — Cathy Kingdon Worley
(74) Attorney, Agent, or Firm — Amy Krom

(57) ABSTRACT

In one aspect, the present invention provides an expression cassette comprising a promoter operably linked to a nucleic acid molecule of interest, which is operably linked to a terminator, further comprising a heterologous intron that enhances expression of the nucleic acid molecule of interest, wherein the heterologous intron is selected from the group comprised of SEQUENCE ID NO. 1 (iZm10430-02), SEQUENCE ID NO. 2 (iZm10430-01) SEQUENCE ID NO. 3 (iZm008975-01), SEQUENCE ID NO. 4 (iZm005854-01), SEQUENCE ID NO. 5 (iZm010719-01), and SEQUENCE ID NO. 6 (iZm007840-01). In another aspect, the present invention provides an expression cassette comprising a promoter operably linked to a nucleic acid molecule of interest, which is operably linked to a heterologous terminator that enhances expression of the nucleic acid molecule of interest, wherein the heterologous terminator is selected from the group of SEQUENCE ID NO. 7 (tZmHSP70-01), SEQUENCE ID NO. 8 (tZmUbi158-01), SEQUENCE ID NO. 9 (tZmUbi1-01), SEQUENCE ID NO. 10 (tZmUbi361-01).

9 Claims, No Drawings
Specification includes a Sequence Listing.

```
                         SEQUENCE LISTING

<160> NUMBER OF SEQ ID NOS: 10

<210> SEQ ID NO 1
<211> LENGTH: 696
<212> TYPE: DNA
<213> ORGANISM: Zea mays

<400> SEQUENCE: 1
gtaagcatcc gcgctccctc cctgcgcagc cgatgtctgc agcgtcgtcc tgccgcatct     60 gtgtcttta  atttttttg  gggtcgccgg gtggtgctcg ggggcacggt tcccgcgcga    120
tcggccggtc attcgcggga aacatcgatc cgatgaggcg cgcgcccctc ggcgcgtccg    180
ccgcgggcgg gtccagttcg tcaaggctcg gtcgcggagt ggatttgggg tgagaggtgc    240
ggttttcgct gggtttcggg tcgggatttg gggttagttg cgggcgtgtg gcgatctgtt    300
```

```
ctctgaccgg ccgtaatctg gtgcgcaaaa ccaagatttt tttccccgtc ggttgggaat      360
cggcatggtg catccagtga tggggatggg atgctcccct cccttttcct tttgagtgct      420
gattgacgta ttcgattcct cggcaaaggg tgtggtggta gggaagctga ccgtttcttg      480
atggcgatga cgatccatct ccgctgattc tcccctcttt ttacctctat tggtcgccga      540
ccctggccat gcccagtgtt agttagtttg tccttttggc gatgttggta gatggctatg      600
gataggttgc tagagtgaga ttgatgtgta ttctttgcca tgttcgttgc tgctcttat       660 actgatgaac gattgtaact gtgtctgcat gtggag                                696

<210> SEQ ID NO 2
<211> LENGTH: 696
<212> TYPE: DNA
<213> ORGANISM: Zea mays

<400> SEQUENCE: 2
gtaagcatcc gcgctccctc cctgcgcagc cgatgtctgc agcgtcgtcc tgccgcatct       60
gtgtctttta atttttttg gggtcgccgg gtggtgctcg ggggcacggt tcccgcgcga      120
tcggccggtc attcgcggga aacatcgatc cgatgaggcg cgcgcccctc ggcgcgtccg      180
ccgcgggcgg gtccagttcg tcaaggctcg gtcgcggagt ggatttgggg tgagaggtgc      240
ggttttcgct gggtttcggg tcgggatttg gggttagttg cgggcgtgtg gcgatctgtt      300
ctctgaccgg ccgtaatctg gtgcgcaaaa ccaagatttt tttccccgtc ggttgggaat      360
cggcatggtg catccagtga tggggatggg atgctcccct cccttttcct tttgagtgct      420
gattgacgta ttcgattcct cggcaaaggg tgtggtggta gggaagctga ccgtttcttg      480
atggcgatga ggatccatct ccgctgattc tcccctcttt ttacctctat tggtcgccga      540
ccctggccat gcccagtgtt agttagtttg tccttttggc gatgttggta gatggctatg      600
gataggttgc tagagtgaga ttgatgtgta ttctttgcca tgttcgttgc tgctcttat       660 actgatgaac gattgtaact gtgtctgcat gtggag                                696

<210> SEQ ID NO 3
<211> LENGTH: 1648
<212> TYPE: DNA
<213> ORGANISM: Zea mays

<400> SEQUENCE: 3
gtgcgtcttg acggccggat tcggctcccc ctcgcgcgcc ctgctcccca aaggcgccgc       60
ctttgctctg atccgtcgct ctgcgcgctc gtggctgctt gtgatctctc ctctgcgggg      120
cggtttcccg gccggttact atcgcggggg gcggaactg ggtcgctggg ccgtggttct       180
tggtgtcccg gagcgccgaa tctggcgccc ctggaggagg agcgtgggag ggtctcccgc      240
gccacgcccg cggccggtcg atccggaatt cgttcagttc gtctgcttag gctgtcttct      300
ttttcaactc cttgcgaaat tcgtagcatc tggagcttgg ggaaagttcc gtcgtgtgat      360
ctaatcccgt gctttttttc cttcggtttg ttcgagggaa acgttcttct gcttcggtat      420
tttggtcgtc tgttgcaagc aagcaatttc tggttttcag gtgtccggga agcagcgtta      480
ctgtccccat cgccgtcggg gattagggga aaattgcgcc ttttcctttc tttttgcaag      540
ctgtgtccca ctccatactg gcttcgattg gattggattg gatagatagc tcgtccgtgg      600
cgtggcacag tgtagcattg atagcccagc ggagtgatgc ttcgctgctg aagcaatcgc      660
aggtttggcg gagctaagga aagagctgta gcgagcacga tgttagcctt ttgaattggc      720
ctggccctgt tccatgagct ggcgtgtgtg agaatggcgt gagtgtgagc tgtgggcacg      780
```

```
aggggaaagg tgagaccccc cttggtgctg gactgctggt gctgtggggg gagcggcagt      840
gcatgagatg catgtgatgc ggcattaaat tttagtgtag ccacgattga gatgaatcta      900
taggtgaagc gaatgaagtg actaatgtgg tttcatcaga ctcaggaatt tgttagtatt      960
cgtccattgc caaagctgac tggtggatgt ttaatctagt cgtagcaata gatttccaac     1020
caatgtgtgt aattattgtc tcgagctaag gtggcaagaa acttatggcg tattaagaat     1080
tgtccaaggt tttccatgca gaatgagctg ttctttgatc agcttcgtag caactggtga     1140
cttgagtagt tagtaccttc ctgccacgta tattttaatc tacctggggt ggttgggaaa     1200
caataaagga caaggattg cataaatcgt ttgcatcatg tgggtcaaat ttggttgccg      1260
tgcacctgtg ttagtctcac atttggtatg tgaagataat gaatgcggaa ctgcagacag     1320
gggagaaggg gtagagagaa tttgtacatg gtcttgtttg gtgcaatgag tgcatgaccc     1380
ttgtaaccag gttcctggat caatgaggtc gaagaacgga acatggtac gtggtaagat      1440 actttaaacg agattttaac actacgtgga cgaaattgtt cccatgttcc cggaacgagg     1500
aacgtggcgg tttctaagtg catgacattg atatcggtta cttaatggaa ttggttgctt     1560
gctttctaag tgatttcgtt tcctttgttc gttttttctga ccggtgctat attgctgccg    1620
cctctaataa aaatgtgttt gatttcag                                        1648

<210> SEQ ID NO 4
<211> LENGTH: 1969
<212> TYPE: DNA
<213> ORGANISM: Zea mays

<400> SEQUENCE: 4
gtgagtcggt gcgcgacccc tcccctcctc aggtcgattc ccactcccct ccacctgcgg       60
attcccatgg cgcaaggacg tggttcgctg atccgcttgc cggatctacg cccttcgctc      120
catccggtta attgtagcct tttgtaccca ggccgcgcgg cgctgccgta ggttcgatac      180
cctgctgtac ttgtcactgg gatagattgc ggtggtttta cgcctcattg gatattccca      240
aatggttatg gacectacta gaggcctgcg attaatagcg actaatcgtc cgattagttt      300
aggaacgatc agcctggctg gctggattga aatttcggcc cagtggccca cttcacttgc      360
ccagcggccc agcccagctt cccttttccc gattcccacc acgtgagcag aagctgcaca      420
accaagaggc aagagccaac agagcgcaga agctgcacaa ccaagaggta agagccaacc      480
gagcaacgaa cgcccaggca cacgagac acgacacgaa ccaggcaacc agctgccgag       540
ggaggaaccc tagcggaaca ctgtgcaggt gacggcggcg cgctaccggt gacggggat       600 acggcggcat cgtcccctc ggccctcct ccatccccgg cgcggcggcg ccagcagccg        660
gcctgcaggt acgtctcca gtctccagaa tccagattca gagcttgtcc ctgttttctg       720
gtgtgctctg ttgtgctgta gcctgtaggt acgggcgttt ggctgttggc ctgttgctgc      780
ccatgtccat gtttgttggt tttcagtttt acttagatgc tgaaagcctg aaaccttcca      840
gtgattattt gcttcatgtt gtagtatggc tgttggcctg ttgctgcccg tgtccatggg      900
catatcacgt atggctgttt gccttgtcga aagcctgaac ctgaagccat gtccatgggc      960
gtgtagttat atatatgaag gttgatcggt tcctatagcc ctggacgatc aggatgtctg     1020
attgaccaat cagagcccgg ttaatcgggc tggtcatcga ctaatcgtga ttagtcggct     1080
gatcgcccct ctggcgatca ggagcgatca gccgatctga aaacattgcg atctccctat     1140
gccgatctcc ctccggctct gaaatttaat actgcagcaa ggtccaaact cagcctgggt     1200
```

| | |
|---|---|
| gattccaact cagcttggaa tcacaattta gcgtgggtga ttccaaactc gacctgggtg | 1260 |
| gttaatcgct ttaccaacca tccgtgagta caataactac ttgcaagaca ggtataattt | 1320 |
| tgaagtcact tggttcagac ttaaagttgc tttgcagtaa tcagtatgca gttgggatgg | 1380 |
| cccatttcat ctcaacatca ttgttattcc aatagcggca attttgcatg atcagtctgc | 1440 |
| tgagtggcga cttttcaaac tgtgacggtc atcagtatcc ggaaggggag gatggcgtcg | 1500 |
| gcgaagtaag aacagccggc ggcgctgtgc caagctgtgc tcagctcaaa gaaatagcca | 1560 |
| gtctcggtct ccagttctcg tctccagtca aggtgataaa aaaagacatg ggtagaacgg | 1620 |
| tccgtgaggc ttactggcct gaggaaagga acacaaaac atttaaaatg aagataagga | 1680 |
| ccaaaaacac ctagaatgaa aaatccgtga gccatggtgt caatttctaa aaggatgatg | 1740 |
| aattggatcc tttatgttga gaggcagccg aattgagacg tgtatactga aatttctccc | 1800 |
| ttgagcatcg atgtacataa aaaatgcttt ttgtatgatt tagtgttacg tcgagatcat | 1860 |
| ggatgcatca ctttctgct gctccttggg tcctcatgta attgggcatc tactgtgtgg | 1920 |
| caacattttt gtatgactga atggtttccc cacctcttta tctctgaag | 1969 |

<210> SEQ ID NO 5
<211> LENGTH: 792
<212> TYPE: DNA
<213> ORGANISM: Zea mays

<400> SEQUENCE: 5

| | |
|---|---|
| gtacgcccat cctctgctgt actccccccg ttcctgctgt gcgaaaccga gcacccaaac | 60 |
| cctagcctaa gctattcgca tcgcaaactc tattgagcga cggatcgcga aacgcgcgcc | 120 |
| gccgcattcg gacgagacct cgtggcccgt accttcctac tctaccgtcg tcgccggaga | 180 |
| cgagctcacc ggttagggtt tcgggattag gggcttgggg cttggattcc cgggggactc | 240 |
| cataccggt ggccttagaa ggggaagggg gcccagcggt ggtggtggtt cgactgtcag | 300 |
| cgagcgagac ggcggggcac cgccgatcgg gcgtcgctgg acatttgatt gagctgggca | 360 |
| ggcgaaggcg tggagcttgc tcttcgattg ggattagagg agggcggagg tggtatggtg | 420 |
| ggcggctcgg ctggctcaat ggagccgctg gccggtggtg gggcaggcga gatcacgctc | 480 |
| tctcatagag cgtaatgggt tgcgtaacac actcctgttt gtatttggat ccgatctaat | 540 |
| aattaaagtt tatttacgtg gtgcacatgt agaattttcc catgcccact gctaacttgg | 600 |
| attggatttt tgccaaaaaa acgggtgtgc acccaatcac ttatagtgaa accgttgtgt | 660 |
| gtttgatgtg cttctaacca agtacaaatc cagtgaaaac acacctacca ttcaacaatc | 720 |
| cacattttgg ttgcaattat cagcattcta gaaaggtgca tgtgcccatt gatacacttg | 780 |
| ctattggtgc ag | 792 |

<210> SEQ ID NO 6
<211> LENGTH: 602
<212> TYPE: DNA
<213> ORGANISM: Zea mays

<400> SEQUENCE: 6

| | |
|---|---|
| ctacagacag agccatccca aagaagcgcc aattgagaac ggaatctatc ttattcttac | 60 |
| gctgaaagaa gcaatcgcaa cgccgcgggc taccataaaa tccactcgcc ataataaaga | 120 |
| gcaatagcgg cagaaaagact gccctgcctg cctcgcccctt atgttccaat cccacggacg | 180 |
| cacggcacgg catatagaag gaaggaacta ggaaggcaca gaggtcccac ccagagcggc | 240 |
| gcacgcagca agttgtcgtg aaatgggagg gaaaatgcta cgggaagcag gaagctaccg | 300 |

-continued

| | |
|---|---|
| ggtgcgggcg gggttctctg agaaatgggc cagagaaggc ggcagccaac cacccccacg | 360 |
| gctccaggcc tccacccacc ccgccgctac cgctaggcgg gcggggcgaa atcccacgcc | 420 |
| gcaatcgagc aaggcggcct aacgcggggg gccatgccga cccggaggca ccagattccc | 480 |
| gcgctcgcaa gccgcagccc gcaggcgacg acacggccac cgggcgcgaa gcaggcagcg | 540 |
| ggaatcacgc acgcagacct cggaagcagc agcaaaagca gagcgcggac gcgagcacgt | 600 |
| ac | 602 |

<210> SEQ ID NO 7
<211> LENGTH: 994
<212> TYPE: DNA
<213> ORGANISM: Zea mays

<400> SEQUENCE: 7

| | |
|---|---|
| gcggtttgtt gtcagtcttg agtgtgctgc agttgctggc tggcccagtt gctgccgaga | 60 |
| gttatcgtca gttggtgcgg tgtgtccgct taaactttat ttgtggttgg ttggtacttt | 120 |
| tgtggtggtt attttttttgg acctcgtgat agtcggtcgg ttcaatgtta tcgcggctac | 180 |
| tggcaaacct taagtgatac ggtattcttc ttttcggtat ttgtttctgc atactgctgg | 240 |
| ctcgtatttt gttttgagc ttgcgattct ttgttaattt caacctttg ccagttagga | 300 |
| ggccattctc atttgattgt ttaccacaat ttttaggctg tcatgttatg tggcatttaa | 360 |
| tgaaattgat aaactcccac ccagaatagc tagcagcttt tgttgggtcc tggttttttct | 420 |
| tgtcctcgaa gagttttggg agcaaaacgg tttctttata tttttttttttc ctcaatacct | 480 |
| cattatgtcc gaaatctttc tccgctagta tctgtactct gtgcagagat ttttcttaaa | 540 |
| ttctttatac ctactacctt aataaaacac tctcgtccat aaatgttggt cattttttgtt | 600 |
| cttactatgt tcttatgtca gaaatctttc tcccccagtt tttcaactct gtgcagagct | 660 |
| ttttcttaaa ttcattatac ctactacctc tataaaatac tctcgtccat aaatgttggc | 720 |
| catttttatt tttaaggagt caaacatttt taactttgat ataagaaatt ttaatattta | 780 |
| tagtataaaa tttatatcag atctttgaat ctccttttat aatgttacaa taaaattatt | 840 |
| ttataatttt agttaaaatt aagaaagttt aattgacacg aacaacatgt cgacaaacat | 900 |
| ttatcgatga aggaagtacc atctctctta cattaccatt tttaacagga cttataaaat | 960 |
| accatctctt ttacacgact aacatataaa gcag | 994 |

<210> SEQ ID NO 8
<211> LENGTH: 1000
<212> TYPE: DNA
<213> ORGANISM: Zea mays

<400> SEQUENCE: 8

| | |
|---|---|
| gccaaggttc atttaagctg ctgctgtacc tgggtatctg cgtcgtctgg tgccctctgg | 60 |
| tgtacctcta tatggatgtc gtcgtctaat aaacatctgt ggtttgtgtg tcatgaatcg | 120 |
| tggttgtggc ttcgttggtt taatggacct gttgtgtcct ctgtgttgta cccaaaactc | 180 |
| ttctgcagca gtatggcttg aatccttatg aagtttgata tttgaacttaa aaagtctgct | 240 |
| cattatgttt ttttctggtt atatctccta attaactgcc tgggatcaaa tttgattcgc | 300 |
| tggtgtttat tggacccctc ccaggttctt gctttctacc gtttcttgct gaatgttaac | 360 |
| ttgattctgt caggctcagt ttcccactat ggcttacagc ttaacgtgtt tggtttgttg | 420 |
| aatgttaact tggttttgtc aagctcagtt ttttactctg gcttacagca taacatgttt | 480 |

| | |
|---|---|
| gacttttggt tttgctgctt tgttattggg ttctgggtag ttcttgatga atccaaaaga | 540 |
| tcatgtgcac agccatatta tctatttaag cgatccaggt tattactatg aaaggatgcc | 600 |
| ttctagctaa ggagtagtta ggttttttct tcaaggttaa attttctcga tgctctagtg | 660 |
| ttcctgtgac cataatcata ataattcctt tgaaagctct atggtccctg aagcagggc | 720 |
| atacaatgca agacagcaac ttgatcacat caactgaagt atacagggtt ctcttaactc | 780 |
| ttggtgactt cggtttaatg gaccggttgt actcgtgttc tatccgtaac cgttgtgatg | 840 |
| tcttgtgtgt ttggttgcgg gatagctggg accacgacgt ttccgtctaa ttctgatgga | 900 |
| tagctataga cggcactgag atggttatat tataacctct gatcctgaac tctacgagat | 960 |
| cgtctcatcc gtcattgcca ccaaatacac cattaaatta | 1000 |

<210> SEQ ID NO 9
<211> LENGTH: 1001
<212> TYPE: DNA
<213> ORGANISM: Zea mays

<400> SEQUENCE: 9

| | |
|---|---|
| gccatcagtc gttgaagctg ctgctgtatc tgggttatct agtgtctctg ccattgccca | 60 |
| aggatggtgc tgtcttttcaa agtatttgta tggtttgtgt cgtgagtcgt gactgagctg | 120 |
| gtttcatgga ccagttgtgt tctcgttacc caaaactatc gtgcgaccgc atatggctta | 180 |
| atcatgaata aatgttgttt gaatttaaac tattcgctga atattgttgt tttttgtcat | 240 |
| gtcagttaat gttactaaat tggttgcctt ctaattttg tttactggtg tttgtcgcac | 300 |
| cttatctttt tactgtatgt ttacttcagg ttctggcagt ctcatttttt gtgactagtt | 360 |
| aaaacttaca gctaaaaaaa tgcagttttt cattttcatt tgaagtttga ttagagctat | 420 |
| tgatacccgg accatcaggt taggttagtt gtgcatagaa tcataaatat taatcatgtt | 480 |
| ttctatgaat taagtcaaac ttgaaagtct ggctgaatat agtttctatg aatcatattg | 540 |
| atatacatgt ttgattattt gttttgctat tagctattta ctttggtgaa tctatatagg | 600 |
| cttatgcaga accttttttt ttgttctata tatccatatc ctagtactca gtagctctat | 660 |
| gttttctgga gactagtggc ttgcttttc gtatgtctaa ttttttgctt gaccattgca | 720 |
| aaacaaaaat tacctagtgt aatctctttt tataataatc ttgtaatgcg tctacctata | 780 |
| ggtcaaagta ggttttgttt ggaacccttg agctaactg ttagctagtt gataaattat | 840 |
| tagctgagtt aagctagcta atgaactagt tttgatatta gctgaggatg tttgaaacct | 900 |
| aataattatt ttttattagc taactatact aaatttagt agagagattc caaacaggag | 960 |
| ttaacatggg atcagattgg ctatgcgttt gcaatcccat a | 1001 |

<210> SEQ ID NO 10
<211> LENGTH: 1035
<212> TYPE: DNA
<213> ORGANISM: Zea mays

<400> SEQUENCE: 10

| | |
|---|---|
| gtcatgggtc gtttaagctg ccgatgtgcc tgcgtcgtct ggtgccctct ctccatatgg | 60 |
| aggttgtcaa agtatctgct gttcgtgtca tgagtcgtgt cagtgttggt ttaataatgg | 120 |
| accggttgtg ttgtgtgtgc gtactaccca gaactatgac aaatcatgaa taagtttgat | 180 |
| gtttgaaatt aaagcctgtg ctcattatgt tctgtctttc agttgtctcc taatatttgc | 240 |
| ctgcaggtac tggctatcta ccgtttctta cttaggaggt gtttgaatgc actaaaacta | 300 |
| atagttagtg gctaaaatta gttaaaacat ccaaacacca tagctaatag ttgaactatt | 360 |

```
agctattttt ggaaaattag ttaatagtga ggtagttatt tgttagctag ctaattcaac      420
taacaatttt tagccaacta acaattagtt tcagtgcatt caaacacccc cttaatgtta      480
acgtggttct atctaccgtc tcctaatata tggttgattg ttcggtttgt tgctatgcta      540
ttgggttctg attgctgcta gttcttgctg aatccagaag ttctcgtagt atagctcaga      600
ttcatattat ttatttgagt gataagtgat ccaggttatt actatgttag ctaggttttt      660
tttacaagga taaattatct gtgatcataa ttcttatgaa agctttatgt ttcctggagg      720
cagtggcatg caatgcatga cagcaacttg atcacaccag ctgaggtaga tacggtaaca      780
aggttcttaa atctgttcac caaatcattg gagaacacac atacacattc ttgccagtct      840
tggttagaga aatttcatga caaaatgcca aagctgtctt gactcttcac ttttggccat      900
gagtcgtgac ttagtttggt ttaatggacc ggttctccta gcttgttcta ctcaaaactg      960
ttgttgatgc gaataagttg tgatggttga tctctggatt ttgttttgct ctcaatagtg     1020
gacgagatta gatag                                                      1035
```

METHODS AND COMPOSITIONS FOR EXPRESSION CASSETTES COMPRISING A MAIZE GENE-DERIVED INTRON FOR ENHANCED EXPRESSION

RELATED APPLICATION INFORMATION

This application claims the benefit of U.S. Application No. 62/269,320, filed 18 Dec. 2015, the contents of which are incorporated herein by reference herein.

STATEMENT REGARDING ELECTRONIC SUBMISSION OF A SEQUENCE LISTING

A Sequence Listing in ASCII text format, submitted under 37 C.F.R. § 1.821, entitled 80678-US-REG-ORG-NAT-1_Sequence_Listing_ST25, 14.5 kb in size, generated on 8 Dec. 2016 and filed via EFS-Web is provided in lieu of a paper copy. This Sequence Listing is hereby incorporated by reference into the specification for its disclosures.

FIELD OF THE INVENTION

The present invention includes expression cassettes that contain regulatory sequences that comprise a substituted intron and/or terminator for enhanced expression of a nucleic acid of interest (NOI) in plants.

BACKGROUND OF THE INVENTION

In agricultural biotechnology, plants can be modified according to one's needs. One way to accomplish this is by using modern genetic engineering techniques. For example, by introducing a nucleic acid molecule of interest (NOI) into a plant, the plant can be specifically modified to express a desirable phenotypic trait. For this, plants are transformed most commonly with an expression cassette that comprises a promoter, a nucleic acid molecule of interest, and a terminator.

Plant gene based expression cassettes typically control spatial and temporal transcription, an important aspect of trait gene development. However, they are often not capable of producing adequate trait protein, limiting and sometimes eliminating their utility. Many factors affect expression of nucleic acids including chromatin structure, transcription efficiency, transcription factors, mRNA stability and regulatory factors such as promoters, enhancers and silencers. In addition, introns are known to affect expression levels in eukaryotes and in some cases may have a larger influence than, for instance, promoters. (Rose et al. Plant Cell 20:543-551 (2008)). Thus, for example, efficiently spliced introns boost expression more than 10-fold while others have little or no effect (Id.). The first intron of maize shrunken-1 gene has been shown to increase gene expression 1000 fold in maize protoplasts (Maas et al. Plant Mol. Biol. 16(2):199-207 (1990)) and the first intron of rice rubi3 enhanced gene expression about 3-fold in stable transgenic rice (Lu et al. Mol. Genet. Genom. 279(6):563-572 (2008)). The effect of introns on increasing nucleic acid expression is termed intron-mediated enhancement (IME) (Id.). Despite the significant influence of introns on the expression of nucleic acids, little is known about the mechanism IME. Further, only a few introns (mostly first introns) have been evaluated experimentally and are known to enhance gene expression in plants. Little is known about the effect of terminator sequences.

Important aspects of the present invention are based on the identification of introns and terminators that can enhance expression of a NOI when substituted into an expression cassette as a heterologous sequence.

SUMMARY OF THE INVENTION

In one aspect, the present invention provides an expression cassette comprising a promoter operably linked to the nucleic acid molecule of interest, which is operably linked to a terminator, further comprising a heterologous intron that enhances expression of the nucleic acid molecule of interest, wherein the heterologous intron is selected from the group comprised of SEQUENCE ID NO. 1 (iZm10430-02), SEQUENCE ID NO. 2 (iZm10430-01) SEQUENCE ID NO. 3 (iZm008975-01), SEQUENCE ID NO. 4 (iZm005854-01), SEQUENCE ID NO. 5 (iZm010719-01), and SEQUENCE ID NO. 6 (iZm007840-01).

In an additional aspect, the present invention provides a vector (e.g., a recombinant DNA vector) comprising an expression cassette of this invention.

Further provided herein is a transgenic plant cell comprising an expression cassette of this invention, as well as a transgenic plant or progeny thereof comprising the transgenic plant cell of this invention.

In some aspects, the transgenic plant or progeny thereof can be a monocot plant. In some aspects, the transgenic plant or progeny thereof of this invention can be a dicot plant. Nonlimiting examples of a plant of this invention include maize, rice, soybean, sunflower, wheat, tomato, potato, sugarcane, barley, sugarbeet and tobacco.

The present invention also provides seed from the transgenic plant or progeny thereof of this invention.

In yet further aspects, the present invention provides a method of producing a protein in a plant cell comprising introducing an expression cassette and/or vector of this invention into the plant cell under conditions whereby the nucleic acid molecule of interest is expressed to produce the protein, thereby producing the protein in a plant cell.

Also provided herein is a method of producing a transgenic plant, comprising: a) introducing the expression cassette of any of claims 1-2 or the vector of claim 3 into a plant cell; and b) regenerating a plant or progeny thereof from the plant cell.

The present invention additionally provides a plant cell produced by the methods of this invention, as well as a plant or progeny thereof produced by the methods of this invention.

Furthermore, the present invention provides an expression cassette, a plant cell and plant or progeny thereof produced by the corresponding methods of this invention.

In one aspect, the present invention provides an expression cassette comprising a promoter operably linked to the nucleic acid molecule of interest, which is operably linked to a heterologous terminator that enhances expression of the nucleic acid molecule of interest, wherein the heterologous terminator is selected from the group of SEQUENCE ID NO. 7 (tZmHSP70-01), SEQUENCE ID NO. 8 (tZmUbi158-01), SEQUENCE ID NO. 9 (tZmUbi1-01), SEQUENCE ID NO. 10 (tZmUbi361-01)).

In an additional aspect, the present invention provides a vector (e.g., a recombinant DNA vector) comprising an expression cassette of this invention.

Further provided herein is a transgenic plant cell comprising an expression cassette of this invention, as well as a transgenic plant or progeny thereof comprising the transgenic plant cell of this invention.

In some aspects, the transgenic plant or progeny thereof can be a monocot plant. In some aspects, the transgenic plant or progeny thereof of this invention can be a dicot plant. Nonlimiting examples of a plant of this invention include maize, rice, soybean, sunflower, wheat, tomato, potato, sugarcane, barley, sugarbeet and tobacco.

The present invention also provides seed from the transgenic plant or progeny thereof of this invention.

In yet further aspects, the present invention provides a method of producing a protein in a plant cell comprising introducing an expression cassette and/or vector of this invention into the plant cell under conditions whereby the nucleic acid molecule of interest is expressed to produce the protein, thereby producing the protein in a plant cell.

Also provided herein is a method of producing a transgenic plant, comprising: a) introducing the expression cassette of any of claims 1 or 2 or the vector of claim 3 into a plant cell; and b) regenerating a plant or progeny thereof from the plant cell.

The present invention additionally provides a plant cell produced by the methods of this invention, as well as a plant or progeny thereof produced by the methods of this invention.

Furthermore, the present invention provides an expression cassette, a plant cell and plant or progeny thereof produced by the corresponding methods of this invention.

DEFINITIONS

The following definitions and methods are provided to better define the present invention and to guide those of ordinary skill in the art in the practice of the present invention. Unless otherwise noted, terms used herein are to be understood according to conventional usage by those of ordinary skill in the relevant art. Definitions of common terms in molecular biology may also be found in Rieger et al., *Glossary of Genetics: Classical and Molecular*, 5th edition, Springer-Verlag: New York, 1994.

A "coding sequence" is a nucleic acid sequence that is transcribed into RNA such as mRNA, rRNA, tRNA, snRNA, sense RNA or antisense RNA. In some embodiments, the RNA is then translated in an organism to produce a protein.

As used herein the term transgenic "event" refers to a recombinant plant produced by transformation and regeneration of a single plant cell with heterologous DNA, for example, an expression cassette that includes one or more genes of interest (e.g., transgenes). The term "event" refers to the original transformant and/or progeny of the transformant that include the heterologous DNA. The term "event" also refers to progeny produced by a sexual outcross between the transformant and another line. Even after repeated backcrossing to a recurrent parent, the inserted DNA and the flanking DNA from the transformed parent is present in the progeny of the cross at the same chromosomal location. Normally, transformation of plant tissue produces multiple events, each of which represent insertion of a DNA construct into a different location in the genome of a plant cell. Based on the expression of the transgene or other desirable characteristics, a particular event is selected.

"Expression cassette" as used herein means a nucleic acid molecule capable of directing expression of a particular nucleotide sequence in an appropriate host cell, comprising a promoter operably linked to the nucleotide acid molecule of interest (e.g., transgene or NOI), which is operably linked to termination signals. It also typically comprises sequences required for proper translation of the nucleotide sequence. The expression cassette may also comprise sequences not necessary in the direct expression of a nucleotide sequence of interest but which are present due to convenient restriction sites for removal of the cassette from an expression vector. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. Typically, however, the expression cassette is heterologous with respect to the host, i.e., the particular nucleic acid sequence of the expression cassette does not occur naturally in the host cell and must have been introduced into the host cell or an ancestor of the host cell by a transformation process known in the art. The expression of the nucleotide sequence in the expression cassette may be under the control of a constitutive promoter or of an inducible promoter that initiates transcription only when the host cell is exposed to some particular external stimulus. In the case of a multicellular organism, such as a plant, the promoter can also be specific to a particular tissue, or organ, or stage of development. An expression cassette, or fragment thereof, can also be referred to as "inserted sequence" or "insertion sequence" when transformed into a plant.

A "gene" is a defined region that is located within a genome and that, besides the aforementioned coding nucleic acid sequence, comprises other, primarily regulatory, nucleic acid sequences responsible for the control of the expression, that is to say the transcription and translation, of the coding portion. A gene may also comprise other 5' and 3' untranslated sequences and termination sequences. Further elements that may be present are, for example, introns.

"Gene of interest" or 'nucleic acid molecule of interest (NOI)" refers to any gene or NOI which, when transferred to a plant, confers upon the plant a desired characteristic such as antibiotic resistance, virus resistance, insect resistance, disease resistance, or resistance to other pests, herbicide tolerance, improved nutritional value, improved performance in an industrial process or altered reproductive capability. The "gene of interest" or NOI may also be one that is transferred to plants for the production of commercially valuable enzymes or metabolites in the plant.

"Genotype" as used herein is the genetic material inherited from parent plants not all of which is necessarily expressed in the descendant plants.

A "heterologous" nucleic acid sequence is a nucleic acid sequence not naturally associated with a host cell into which it is introduced, including non-naturally occurring multiple copies of a naturally occurring nucleic acid sequence. A nucleic acid sequence can also be heterologous to other nucleic acid sequences with which it may be associated, for example in a nucleic acid construct, such as e.g., an expression vector. As one nonlimiting example, a promoter may be present in a nucleic acid construct in combination with one or more regulatory element and/or coding sequences that do not naturally occur in association with that particular promoter, i.e., they are heterologous to the promoter.

A "homologous" nucleic acid sequence is a nucleic acid sequence naturally associated with a host cell into which it is introduced. A homologous (e.g., nonheterologous) nucleic acid sequence can also be a nucleic acid sequence that is naturally associated with other nucleic acid sequences that may be present, e.g., in a nucleic acid construct. As one nonlimiting example, a promoter may be present in a nucleic acid construct in combination with one or more regulatory elements and/or coding sequences that naturally occur in association with that particular promoter, i.e., they are homologous or nonheterologous to the promoter.

"Operably-linked" refers to the association of nucleic acid sequences on a single nucleic acid sequence so that the function of one affects the function of the other. For example, a promoter is operably-linked with a coding sequence or functional RNA when it is capable of affecting the expression of that coding sequence or functional RNA (i.e., the coding sequence or functional RNA is under the transcriptional control of the promoter). Coding sequences in sense or antisense orientation can be operably-linked to regulatory sequences.

The term "transformation" as used herein refers to the transfer of a nucleic acid molecule into the genome of a host cell, resulting in genetically stable inheritance. In some embodiments, the introduction into a plant, plant part and/or plant cell is via bacterial-mediated transformation, particle bombardment transformation, calcium-phosphate-mediated transformation, cyclodextrin-mediated transformation, electroporation, liposome-mediated transformation, nanoparticle-mediated transformation, polymer-mediated transformation, virus-mediated nucleic acid delivery, whisker-mediated nucleic acid delivery, microinjection, sonication, infiltration, polyethylene glycol-mediated transformation, protoplast transformation, or any other electrical, chemical, physical and/or biological mechanism that results in the introduction of nucleic acid into the plant, plant part and/or cell thereof, or any combination thereof.

Procedures for transforming plants are well known and routine in the art and are described throughout the literature. Non-limiting examples of methods for transformation of plants include transformation via bacterial-mediated nucleic acid delivery (e.g., via bacteria from the genus *Agrobacterium*), viral-mediated nucleic acid delivery, silicon carbide or nucleic acid whisker-mediated nucleic acid delivery, liposome mediated nucleic acid delivery, microinjection, microparticle bombardment, calcium-phosphate-mediated transformation, cyclodextrin-mediated transformation, electroporation, nanoparticle-mediated transformation, sonication, infiltration, PEG-mediated nucleic acid uptake, as well as any other electrical, chemical, physical (mechanical) and/or biological mechanism that results in the introduction of nucleic acid into the plant cell, including any combination thereof. General guides to various plant transformation methods known in the art include Miki et al. ("Procedures for Introducing Foreign DNA into Plants" in *Methods in Plant Molecular Biology and Biotechnology*, Glick, B. R. and Thompson, J. E., Eds. (CRC Press, Inc., Boca Raton, 1993), pages 67-88) and Rakowoczy-Trojanowska (*Cell Mol Biol Lett* 7:849-858 (2002)).

*Agrobacterium*-mediated transformation is a commonly used method for transforming plants because of its high efficiency of transformation and because of its broad utility with many different species. *Agrobacterium*-mediated transformation typically involves transfer of the binary vector carrying the foreign DNA of interest to an appropriate *Agrobacterium* strain that may depend on the complement of vir genes carried by the host *Agrobacterium* strain either on a co-resident Ti plasmid or chromosomally (Uknes et al. 1993, *Plant Cell* 5:159-169). The transfer of the recombinant binary vector to *Agrobacterium* can be accomplished by a tri-parental mating procedure using *Escherichia coli* carrying the recombinant binary vector, a helper *E. coli* strain that carries a plasmid that is able to mobilize the recombinant binary vector to the target *Agrobacterium* strain. Alternatively, the recombinant binary vector can be transferred to *Agrobacterium* by nucleic acid transformation (Höfgen and Willmitzer 1988, *Nucleic Acids Res* 16:9877).

Transformation of a plant by recombinant *Agrobacterium* usually involves co-cultivation of the *Agrobacterium* with explants from the plant and follows methods well known in the art. Transformed tissue is typically regenerated on selection medium carrying an antibiotic or herbicide resistance marker between the binary plasmid T-DNA borders.

Another method for transforming plants, plant parts and plant cells involves propelling inert or biologically active particles at plant tissues and cells. See, e.g., U.S. Pat. Nos. 4,945,050; 5,036,006 and 5,100,792. Generally, this method involves propelling inert or biologically active particles at the plant cells under conditions effective to penetrate the outer surface of the cell and afford incorporation within the interior thereof. When inert particles are utilized, the vector can be introduced into the cell by coating the particles with the vector containing the nucleic acid of interest. Alternatively, a cell or cells can be surrounded by the vector so that the vector is carried into the cell by the wake of the particle. Biologically active particles (e.g., dried yeast cells, dried bacteria or a bacteriophage, each containing one or more nucleic acids sought to be introduced) also can be propelled into plant tissue.

Thus, in particular embodiments of the present invention, a plant cell can be transformed by any method known in the art and as described herein and intact plants can be regenerated from these transformed cells using any of a variety of known techniques. Plant regeneration from plant cells, plant tissue culture and/or cultured protoplasts is described, for example, in Evans et al. (*Handbook of Plant Cell Cultures*, Vol. 1, MacMilan Publishing Co. New York (1983)); and Vasil I. R. (ed.) (*Cell Culture and Somatic Cell Genetics of Plants*, Acad. Press, Orlando, Vol. I (1984), and Vol. II (1986)). Methods of selecting for transformed transgenic plants, plant cells and/or plant tissue culture are routine in the art and can be employed in the methods of the invention provided herein.

By "stably introducing" or "stably introduced" in the context of a polynucleotide introduced into a cell is intended the introduced polynucleotide is stably incorporated into the genome of the cell, and thus the cell is stably transformed with the polynucleotide.

"Stable transformation" or "stably transformed" as used herein means that a nucleic acid is introduced into a cell and integrates into the genome of the cell. As such, the integrated nucleic acid is capable of being inherited by the progeny thereof, more particularly, by the progeny of multiple successive generations. "Genome" as used herein also includes the nuclear and the plastid genome, and therefore includes integration of the nucleic acid into, for example, the chloroplast genome. Stable transformation as used herein can also refer to a transgene that is maintained extrachromasomally, for example, as a minichromosome.

Stable transformation of a cell can be detected by, for example, a Southern blot hybridization assay of genomic DNA of the cell with nucleic acid sequences which specifically hybridize with a nucleotide sequence of a transgene introduced into an organism (e.g., a plant). Stable transformation of a cell can be detected by, for example, a Northern blot hybridization assay of RNA of the cell with nucleic acid sequences which specifically hybridize with a nucleotide sequence of a transgene introduced into a plant or other organism. Stable transformation of a cell can also be detected by, e.g., a polymerase chain reaction (PCR) or other amplification reactions as are well known in the art, employing specific primer sequences that hybridize with target sequence(s) of a transgene, resulting in amplification of the transgene sequence, which can be detected according to standard methods. Transformation can also be detected by direct sequencing and/or hybridization protocols well known in the art.

The "transformation and regeneration process" refers to the process of stably introducing a transgene into a plant cell and regenerating a plant from the transgenic plant cell. As used herein, transformation and regeneration includes the selection process, whereby a transgene comprises a selectable marker and the transformed cell has incorporated and expressed the transgene, such that the transformed cell will survive and developmentally flourish in the presence of the selection agent. "Regeneration" refers to growing a whole plant from a plant cell, a group of plant cells, or a plant piece such as from a protoplast, callus, or tissue part.

As used in the description of the embodiments of the invention and the appended claims, the singular forms "a," "an," and "the" are intended to include the plural forms as well, unless the context clearly indicates otherwise.

As used herein, "and/or" refers to and encompasses any and all possible combinations of one or more of the associated listed items.

The term "about," as used herein when referring to a measurable value such as an amount of a compound, dose, time, temperature, and the like, is meant to encompass variations of 20%, 10%, 5%, 1%, 0.5%, or even 0.1% of the specified amount.

The terms "comprise," "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

The terms "nucleotide sequence" "nucleic acid," "nucleic acid molecule," "oligonucleotide" and "polynucleotide" are used interchangeably herein to refer to a heteropolymer of nucleotides and encompass both RNA and DNA, including cDNA, genomic DNA, mRNA, synthetic (e.g., chemically synthesized) DNA or RNA and chimeras of RNA and DNA. The term nucleic acid refers to a chain of nucleotides without regard to length of the chain. A nucleic acid can be double-stranded or single-stranded. Where single-stranded, the nucleic acid can be a sense strand or an antisense strand. A nucleic acid can be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases. Nucleic acid sequences provided herein are presented herein in the 5' to 3' direction, from left to right and are represented using the standard code for representing the nucleotide characters as set forth in the U.S. sequence rules, 37 CFR §§ 1.821-1.825 and the World Intellectual Property Organization (WIPO) Standard ST.25.

An "isolated" nucleic acid molecule or nucleotide sequence or an "isolated" polypeptide is a nucleic acid molecule, nucleotide sequence or polypeptide that, by the hand of man, exists apart from its native environment and/or has a function that is different, modified, modulated and/or altered as compared to its function in its native environment and is therefore not a product of nature. An isolated nucleic acid molecule or isolated polypeptide may exist in a purified form or may exist in a non-native environment such as, for example, a recombinant host cell. Thus, for example, with respect to polynucleotides, the term isolated means that it is separated from the chromosome and/or cell in which it naturally occurs. A polynucleotide is also isolated if it is separated from the chromosome and/or cell in which it naturally occurs and is then inserted into a genetic context, a chromosome, a chromosome location, and/or a cell in which it does not naturally occur. The recombinant nucleic acid molecules and nucleotide sequences of the invention can be considered to be "isolated" as defined above.

Thus, an "isolated nucleic acid molecule" or "isolated nucleotide sequence" is a nucleic acid molecule or nucleotide sequence that is not immediately contiguous with nucleotide sequences with which it is immediately contiguous (one on the 5' end and one on the 3' end) in the naturally occurring genome of the organism from which it is derived. Accordingly, in one embodiment, an isolated nucleic acid includes some or all of the 5' non-coding (e.g., promoter) sequences that are immediately contiguous to a coding sequence. The term therefore includes, for example, a recombinant nucleic acid that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment), independent of other sequences. It also includes a recombinant nucleic acid that is part of a hybrid nucleic acid molecule encoding an additional polypeptide or peptide sequence. An "isolated nucleic acid molecule" or "isolated nucleotide sequence" can also include a nucleotide sequence derived from and inserted into the same natural, original cell type, but which is present in a non-natural state, e.g., present in a different copy number, and/or under the control of different regulatory sequences than that found in the native state of the nucleic acid molecule.

The term "isolated" can further refer to a nucleic acid molecule, nucleotide sequence, polypeptide, peptide or fragment that is substantially free of cellular material, viral material, and/or culture medium (e.g., when produced by recombinant DNA techniques), or chemical precursors or other chemicals (e.g., when chemically synthesized). Moreover, an "isolated fragment" is a fragment of a nucleic acid molecule, nucleotide sequence or polypeptide that is not naturally occurring as a fragment and would not be found as such in the natural state. "Isolated" does not necessarily mean that the preparation is technically pure (homogeneous), but it is sufficiently pure to provide the polypeptide or nucleic acid in a form in which it can be used for the intended purpose.

In representative embodiments of the invention, an "isolated" nucleic acid molecule, nucleotide sequence, and/or polypeptide is at least about 5%, 10%, 15%, 20%, 25%, 30%, 40%, 50%, 60%, 70%, 75%, 80%, 85%, 90%, 95%, 97%, 98%, 99% pure (w/w) or more. In other embodiments, an "isolated" nucleic acid, nucleotide sequence, and/or polypeptide indicates that at least about a 5-fold, 10-fold, 25-fold, 100-fold, 1000-fold, 10,000-fold, 100,000-fold or more enrichment of the nucleic acid (w/w) is achieved as compared with the starting material.

As used herein, "heterologous" refers to a nucleic acid molecule or nucleotide sequence that either originates from another species or is from the same species or organism but is modified from either its original form or the form primarily expressed in the cell. Thus, a nucleotide sequence derived from an organism or species different from that of the cell into which the nucleotide sequence is introduced, is heterologous with respect to that cell and the cell's descendants. In addition, a heterologous nucleotide sequence includes a nucleotide sequence derived from and inserted into the same natural, original cell type, but which is present in a non-natural state, e.g., present in a different copy number, and/or under the control of different regulatory sequences than that found in the native state of the nucleic acid molecule.

"Wild-type" nucleotide sequence or amino acid sequence refers to a naturally occurring ("native") or endogenous nucleotide sequence or amino acid sequence. Thus, for example, a "wild-type mRNA" is an mRNA that is naturally occurring in or endogenous to the organism. A "homologous" nucleotide sequence is a nucleotide sequence naturally associated with a host cell into which it is introduced.

By the term "express" or "expression" of a polynucleotide coding sequence, it is meant that the sequence is transcribed, and optionally translated.

"Nucleotide sequence of interest" or "nucleic acid molecule of interest" refers to any nucleotide sequence or NOI which, when introduced into a plant, confers upon the plant a desired characteristic such as antibiotic resistance, virus resistance, insect resistance, disease resistance, or resistance to other pests, herbicide tolerance, improved nutritional value, improved performance in an industrial process or altered reproductive capability. The "nucleotide sequence of interest" or NOI may also be one that is transferred to plants for the production of commercially valuable enzymes or metabolites in the plant.

As used herein, the phrases "operably linked," "operatively linked," "operatively associated" or "in operative association" and the like, mean that elements of a nucleic acid construct such as an expression cassette or nucleic acid molecule are configured so as to perform their usual function. Thus, regulatory or control sequences (e.g., promoters) operatively associated with a nucleotide sequence are capable of effecting expression of the nucleotide sequence. For example, a promoter in operative association with a nucleotide sequence encoding miR396c would be capable of effecting the expression of that miR396c nucleotide sequence.

The control sequences need not be contiguous with the nucleotide sequence of interest, as long as they function to direct the expression thereof. Thus, for example, intervening untranslated, yet transcribed, sequences can be present between a promoter and a coding sequence, and the promoter sequence can still be considered "operably linked" to the coding sequence.

As used herein, the terms "transformed" and "transgenic" refer to any plant, plant cell, callus, plant tissue, or plant part that contains all or part of at least one recombinant (e.g., heterologous) polynucleotide. In some embodiments, all or part of the recombinant polynucleotide is stably integrated into a chromosome or stable extra-chromosomal element, so that it is passed on to successive generations. For the purposes of the invention, the term "recombinant polynucleotide" refers to a polynucleotide that has been altered, rearranged, or modified by genetic engineering. Examples include any cloned polynucleotide, or polynucleotides, that are linked or joined to heterologous sequences. The term "recombinant" does not refer to alterations of polynucleotides that result from naturally occurring events, such as spontaneous mutations, or from non-spontaneous mutagenesis followed by selective breeding.

The term "introducing" or "introduce" in the context of a plant cell, plant and/or plant part means contacting a nucleic acid molecule with the plant, plant part, and/or plant cell in such a manner that the nucleic acid molecule gains access to the interior of the plant cell and/or a cell of the plant and/or plant part. Where more than one nucleic acid molecule is to be introduced these nucleic acid molecules can be assembled as part of a single polynucleotide or nucleic acid construct, or as separate polynucleotide or nucleic acid constructs, and can be located on the same or different nucleic acid constructs. Accordingly, these polynucleotides can be introduced into plant cells in a single transformation event, in separate transformation events, or, e.g., as part of a breeding protocol. Thus, the term "transformation" as used herein refers to the introduction of a heterologous nucleic acid into a cell. Transformation of a cell may be stable or transient. Thus, a transgenic plant cell, plant and/or plant part of the invention can be stably transformed or transiently transformed.

The term "plant part," as used herein, includes but is not limited to embryos, pollen, ovules, seeds, leaves, stems, shoots, flowers, branches, fruit, kernels, ears, cobs, husks, stalks, roots, root tips, anthers, plant cells including plant cells that are intact in plants and/or parts of plants, plant protoplasts, plant tissues, plant cell tissue cultures, plant calli, plant clumps, and the like. As used herein, "shoot" refers to the above ground parts including the leaves and stems. Further, as used herein, "plant cell" refers to a structural and physiological unit of the plant, which comprises a cell wall and also may refer to a protoplast. A plant cell of the present invention can be in the form of an isolated single cell or can be a cultured cell or can be a part of a higher-organized unit such as, for example, a plant tissue or a plant organ.

"Transient transformation" in the context of a polynucleotide means that a polynucleotide is introduced into the cell and does not integrate into the genome of the cell.

Transient transformation may be detected by, for example, an enzyme-linked immunosorbent assay (ELISA) or Western blot, which can detect the presence of a peptide or polypeptide encoded by one or more nucleic acid molecules introduced into an organism. Stable transformation of a cell can be detected by, for example, a Southern blot hybridization assay of genomic DNA of the cell with nucleic acid sequences which specifically hybridize with a nucleotide sequence of a nucleic acid molecule introduced into an organism (e.g., a plant). Stable transformation of a cell can be detected by, for example, a Northern blot hybridization assay of RNA of the cell with nucleic acid sequences which specifically hybridize with a nucleotide sequence of a nucleic acid molecule introduced into a plant or other organism. Stable transformation of a cell can also be detected by, e.g., a polymerase chain reaction (PCR) or other amplification reaction as are well known in the art, employing specific primer sequences that hybridize with target sequence(s) of a nucleic acid molecule, resulting in amplification of the target sequence(s), which can be detected according to standard methods. Transformation can also be detected by direct sequencing and/or hybridization protocols well known in the art.

The terms "open reading frame" and "ORF" refer to the amino acid sequence encoded between translation initiation and termination codons of a coding sequence. The terms "initiation codon" and "termination codon" refer to a unit of three adjacent nucleotides ('codon') in a coding sequence that specifies initiation and chain termination, respectively, of protein synthesis (mRNA translation).

The term "abiotic stress" refers to nonliving environmental factors such as frost, drought, excessive heat, high winds, etc., that can have harmful effects on plants.

"Promoter" refers to a nucleotide sequence, usually upstream (5') to its coding sequence, which controls the expression of the coding sequence by providing the recognition for RNA polymerase and other factors required for proper transcription. "Promoter regulatory sequences" consist of proximal and more distal upstream elements. Promoter regulatory sequences influence the transcription, RNA processing or stability, or translation of the associated coding sequence. Regulatory sequences include enhancers, promoters, untranslated leader sequences, introns, and polyadenylation signal sequences. They include natural and synthetic sequences as well as sequences that may be a combination of synthetic and natural sequences. An "enhancer" is a DNA sequence that can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. The meaning of the term "promoter" includes "promoter regulatory sequences."

"Primary transformant" and "T0 generation" refer to transgenic plants that are of the same genetic generation as the tissue that was initially transformed (i.e., not having gone through meiosis and fertilization since transformation). "Secondary transformants" and the "T1, T2, T3, etc. generations" refer to transgenic plants derived from primary transformants through one or more meiotic and fertilization cycles. They may be derived by self-fertilization of primary or secondary transformants or crosses of primary or secondary transformants with other transformed or untransformed plants.

"Intron" refers to an intervening section of DNA which occurs almost exclusively within a eukaryotic gene, but which is not translated to amino acid sequences in the gene product. The introns are removed from the pre-mature mRNA through a process called splicing, which leaves the exons untouched, to form an mRNA. For purposes of the present invention, the definition of the term "intron" includes modifications to the nucleotide sequence of an intron derived from a target gene, provided the modified intron does not significantly reduce the activity of its associated 5' regulatory sequence.

"Exon" refers to a section of DNA which carries the coding sequence for a protein or part of it. Exons are separated by intervening, non-coding sequences (introns). For purposes of the present invention, the definition of the term "exon" includes modifications to the nucleotide sequence of an exon derived from a target gene, provided the modified exon does not significantly reduce the activity of its associated 5' regulatory sequence.

"iMeter score" as used herein meansIME=Intron Mediate Enhancement. From Rose, et al Plant Cell 2008, v20, p 543-551, The IMEter score is a product of a work-based discriminator called IMEter. The IMEter reports a log-odds score based on the frequencies of all possible words (nucleotide sequences of a given length); a positive score indicates the input sequence is similar to proximal introns, and a negative score indicates similarity to distal introns.

The terms "minimum free energy" (MFE), "free energy score," and "Gibbs free energy" are used herein interchangeably. The Gibbs free energy is a thermodynamic quantity that is the difference between the enthalpy and the product of the absolute temperature and the entropy of a system. Gibbs free energy is the capacity of a system to do non-mechanical work and $\Delta G$ measures the non-mechanical work done on it. (Perrot, Pierre. A to Z of Thermodynamics. Oxford University Press (1998)). The Gibbs free energy is defined as $G=H-TS$, where H is the enthalpy, T is temperature and S is the entropy ($H=U+pV$, where p is the pressure and V is the volume).

It is generally considered that all systems strive to achieve a minimum free energy. Thus, when the change in Gibbs free energy, $\Delta G$, is negative then a reaction is favored and energy is released. The amount of energy released is equal to the maximum amount of work that can be performed as a result of that particular chemical reaction. When conditions result in a change in Gibbs free energy, $\Delta G$, that is positive then energy must be added to the system to make the reaction proceed. In isothermal, isobaric systems, Gibbs free energy is a representative measure of the competing effects of enthalpy and entropy that are involved in a thermodynamic process. Thus, Gibb free energy can be consider to be a dynamic quantity.

Accordingly, as used herein, minimum free energy (i.e., free energy, Gibbs free energy) identifies the value for the structure found by thermodynamic optimization (i.e., an implementation of the Zuker algorithm (M. Zuker and P. Stiegler, Nucleic Acids Research 9:133-148 (1981)) that has the lowest free energy value (i.e., Gibb's free energy; $\Delta G$ (kcal/mol); $\Delta G$/length of nucleotide sequence (kcal/mol/base pair)). The Gibb's free energy of a sequence can be calculated using, for example, the RNAfold program as known by those of skill in the art. (See, e.g., Id., Hofacker et al. Monatshefte f. Chemie 125: 167-188 (1994); McCaskill J S. Biopolymers 29 (6-7):1105-19. (1990); and Hofacker et al. Bioinformatics 22 (10):1172-6 (2006)).

It is noted that the measurement of free energy can be biased by nucleotide sequence length. Longer nucleotide sequences have a greater range of free energies than short nucleotide sequences. Thus, nucleotide sequences of variable length can be compared by normalizing the free energy calculation (kcal/mol) by dividing the free energy by the sequence length (i.e., the mean free energy=$\Delta G$/length of nucleotide sequence (kcal/mol/base pair)).

The ViennaRNA package version 1.8.2 is used to calculate the free energy for each input sequence. (Hofacker et al. Monatshefte f. Chemie 125: 167-188 (1994); tbi.uni-vie.ac.at/RNA/). The parameter settings for calculation were "-p0-d2," which turns on calculation of the partition function and ensures that the partition function and the minimum free energy treat dangling end energies in the same manner. Calculation of the energies was executed on the in-house Linux cluster. In this manner, the free energy value and free energy per base pair were determined for each intron. The free energy score refers to the delta-G reported by the tool. The following reference is provided for background on how free energies are calculated: Expanded Sequence Dependence of Thermodynamic Parameters Improves Prediction of RNA Secondary Structure J. Mol. Biol. 288, 911-940 (1999).

DETAILED DESCRIPTION OF THE INVENTION

The present invention includes a number of different aspects, including enhancing transgene or NOI expression in plants, by identifying introns and terminators that impart improved or enhanced protein production by an expression cassette when the intron and/or terminator is incorporated into that expression cassette as a heterologous sequence. The most common way to incorporate an intron and/or terminator is by replacement of the "native" intron and/or "native" terminator with an intron and/or terminator, respectively, identified according to the methods described herein to be an intron and/or terminator that enhances transgene expression. These heterologous components act to increase trait gene (e.g., transgene or NOI) expression and protein production.

In one aspect, the present invention provides an expression cassette comprising a promoter operably linked to the nucleotide sequence of interest, which is operably linked to a terminator, further comprising a heterologous intron that enhances expression of the nucleotide sequence of interest, wherein the heterologous intron is selected from the group comprised of SEQUENCE ID NO. 1 (iZm10430-02), SEQUENCE ID NO. 2 (iZm10430-01) SEQUENCE ID NO. 3 (iZm008975-01), SEQUENCE ID NO. 4 (iZm005854-01), SEQUENCE ID NO. 5 (iZm010719-01), and SEQUENCE ID NO. 6 (iZm007840-01).

In an additional aspect, the present invention provides a vector (e.g., a recombinant DNA vector) comprising an expression cassette of this invention.

Further provided herein is a transgenic plant cell comprising an expression cassette of this invention, as well as a transgenic plant or progeny thereof comprising the transgenic plant cell of this invention.

In some aspects, the transgenic plant or progeny thereof can be a monocot plant. In some aspects, the transgenic plant or progeny thereof of this invention can be a dicot plant. Nonlimiting examples of a plant of this invention include maize, rice, soybean, sunflower, wheat, tomato, potato, sugarcane, barley, sugarbeet and tobacco.

The present invention also provides seed from the transgenic plant or progeny thereof of this invention.

In yet further aspects, the present invention provides a method of producing a protein in a plant cell comprising introducing an expression cassette and/or vector of this invention into the plant cell under conditions whereby the nucleic acid molecule of interest is expressed to produce the protein, thereby producing the protein in a plant cell.

Also provided herein is a method of producing a transgenic plant, comprising: a) introducing the expression cassette of any of claims 1-2 or the vector of claim 3 into a plant cell; and b) regenerating a plant or progeny thereof from the plant cell.

The present invention additionally provides a plant cell produced by the methods of this invention, as well as a plant or progeny thereof produced by the methods of this invention.

Furthermore, the present invention provides an expression cassette, a plant cell and plant or progeny thereof produced by the corresponding methods of this invention.

In one aspect, the present invention provides an expression cassette comprising a promoter operably linked to the nucleotide sequence of interest, which is operably linked to a heterologous terminator that enhances expression of the nucleotide sequence of interest, wherein the heterologous terminator is selected from the group of SEQUENCE ID NO. 7 (tZmHSP70-01), SEQUENCE ID NO. 8 (tZmUbi158-01), SEQUENCE ID NO. 9 (tZmUbi1-01), SEQUENCE ID NO. 10 (tZmUbi361-01)).

In an additional aspect, the present invention provides a vector (e.g., a recombinant DNA vector) comprising an expression cassette of this invention.

Further provided herein is a transgenic plant cell comprising an expression cassette of this invention, as well as a transgenic plant or progeny thereof comprising the transgenic plant cell of this invention.

In some aspects, the transgenic plant or progeny thereof can be a monocot plant. In some aspects, the transgenic plant or progeny thereof of this invention can be a dicot plant. Nonlimiting examples of a plant of this invention include maize, rice, soybean, sunflower, wheat, tomato, potato, sugarcane, barley, sugarbeet and tobacco.

The present invention also provides seed from the transgenic plant or progeny thereof of this invention.

In yet further aspects, the present invention provides a method of producing a protein in a plant cell comprising introducing an expression cassette and/or vector of this invention into the plant cell under conditions whereby the nucleic acid molecule of interest is expressed to produce the protein, thereby producing the protein in a plant cell.

Also provided herein is a method of producing a transgenic plant, comprising: a) introducing the expression cassette of any of claims 1 or 2 the vector of claim 3 into a plant cell; and b) regenerating a plant or progeny thereof from the plant cell.

The present invention additionally provides a plant cell produced by the methods of this invention, as well as a plant or progeny thereof produced by the methods of this invention.

Furthermore, the present invention provides an expression cassette, a plant cell and plant or progeny thereof produced by the corresponding methods of this invention.

Thus, in one aspect, the present invention provides a method of identifying an intron that enhances expression of a nucleic acid molecule of interest in an expression cassette, comprising: a) calculating the delta-G for a multiplicity of respective first introns from a multiplicity of respective genes in the genome of a plant; b) selecting from the multiplicity of first introns a first subset of candidate introns with the lowest delta-G; c) selecting from the first subset of candidate introns a second subset of candidate introns from highly transcribed constitutively expressed genes; d) producing a first expression cassette comprising a promoter operably associated with a heterologous intron and further comprising a nucleic acid molecule of interest encoding a protein, wherein the nucleic acid molecule of interest is operably associated with the promoter and the heterologous intron and wherein the heterologous intron is a candidate intron of the second subset of candidate introns; e) measuring production of the protein encoded by the nucleic acid molecule of interest in the first expression cassette; and f) measuring production of the same protein encoded by the same nucleic acid molecule of interest of (e) in a second expression cassette comprising the same promoter as the first expression cassette operably associated with a non-heterologous intron, wherein an amount of protein measured in (e) that is greater than an amount of protein measured in (f) identifies the candidate intron as an intron that enhances expression of a nucleic acid molecule of interest in an expression cassette, wherein the enhancement is relative to expression of the nucleic acid molecule of interest in an expression cassette comprising a promoter operably associated with a non-heterologous intron. In some embodiments, the nucleic acid molecule of interest can encode a reporter protein. In other embodiments, the nucleic acid molecule can encode a protein that imparts a desirable phenotype in the plant (e.g., insect or pest resistance or tolerance, biotic or abiotic stress tolerance, drought tolerance, heat tolerance, cold tolerance, high salt tolerance and/or improved yield, singly or in any combination. In some embodiments, the protein can be a commercially useful protein that is produced in sufficient quantity in the plant cells, collected from the cells and used in a commercial application.

In additional aspects, the present invention provides a method of constructing an expression cassette comprising an intron that enhances expression of a nucleic acid molecule of interest in the expression cassette, comprising the steps of: a) calculating the delta-G score for a multiplicity of respective first introns from a multiplicity of respective genes in the genome of a plant; b) selecting from the multiplicity of first introns a first subset of candidate introns with the lowest delta-G score; c) selecting from the first subset of candidate introns a second subset of candidate introns from highly transcribed constitutively expressed genes; d) producing a first expression cassette comprising a promoter operably associated with a heterologous intron and further comprising a nucleic acid molecule of interest encoding a protein, wherein the nucleic acid molecule of interest is operably associated with the promoter and the heterologous intron and wherein the heterologous intron is a candidate intron of the second subset of candidate introns; e) measuring production of the protein encoded by the nucleic acid molecule of interest in the first expression cassette; f) measuring production of the same protein encoded by the same nucleic acid molecule of interest of (e) in a second expression cassette comprising the same promoter as the first expression cassette operably associated with a non-heterologous intron, wherein an amount of protein measured in (e) that is greater than an amount of protein measured in (f) identifies the candidate intron as an intron that enhances expression of a nucleic acid molecule of interest in an expression cassette, wherein the enhancement is relative to expression of the nucleic acid molecule of interest in an expression cassette comprising a promoter operably associated with a non-heterologous intron; and g) constructing an expression cassette comprising the candidate intron identified in step (f) above, wherein the intron is operably linked to a promoter to which the intron is heterologous and further comprising a nucleotide sequence of interest operably associated with the promoter and the heterologous intron.

In an additional aspect, the present invention provides a method of producing a plant cell comprising an expression cassette comprising an intron that enhances expression of a nucleic acid molecule of interest in the expression cassette, comprising the steps of: a) calculating the delta-G score for a multiplicity of respective first introns from a multiplicity of respective genes in the genome of a plant; b) selecting from the multiplicity of first introns a first subset of candidate introns with the highestdelta-G score; c) selecting from the first subset of candidate introns a second subset of candidate introns from highly transcribed constitutively expressed genes; d) producing a first expression cassette comprising a promoter operably associated with a heterologous intron and further comprising a nucleic acid molecule of interest encoding a protein, wherein the nucleic acid molecule of interest is operably associated with the promoter and the heterologous intron and wherein the heterologous intron is a candidate intron of the second subset of candidate introns; e) measuring production of the protein encoded by the nucleic acid molecule of interest in the first expression cassette; f) measuring production of the same protein encoded by the same nucleic acid molecule of interest of (e) in a second expression cassette comprising the same promoter as the first expression cassette operably associated with a non-heterologous intron, wherein an amount of protein measured in (e) that is greater than an amount of protein measured in (f) identifies the candidate intron as an intron that enhances expression of a nucleic acid molecule of interest in an expression cassette, wherein the enhancement is relative to expression of the nucleic acid molecule of interest in an expression cassette comprising a promoter operably associated with a non-heterologous intron; g) constructing an expression cassette comprising the candidate intron identified in step (f) above, wherein the intron is operably linked to a promoter to which the intron is heterologous and further comprising a nucleotide sequence of interest operably associated with the promoter and the heterologous intron; and h) introducing the expression cassette into the plant cell, thereby producing a plant cell comprising an expression cassette comprising an intron that enhances expression of a nucleic acid molecule of interest in the expression cassette. In some embodiments, this method can further comprise the step of regenerating a plant or progeny thereof from the plant cell of (h).

Further aspects of this invention include an expression cassette produced by the method described above. In some embodiments, the expression cassette can further comprise a terminator sequence that is heterologous to the promoter and operably associated with the nucleic acid molecule of interest. In some embodiments of the expression cassette of this invention, the terminator sequence can be heterologous to the intron.

Also provided herein is an expression cassette comprising a promoter and an intron that is not heterologous to the promoter, operably associated with a nucleic acid molecule of interest encoding a protein, wherein the nucleic acid molecule of interest is operably associated with a terminator sequence that is heterologous to the promoter.

In embodiments of the expression cassettes of this invention in which the intron is heterologous to the promoter, the intron can comprise, consist essentially of, or consist of the nucleotide sequence of SEQUENCE ID NO. 1 (iZm10430-02), SEQUENCE ID NO. 2 (iZm10430-01) SEQUENCE ID NO. 3 (iZm008975-01), SEQUENCE ID NO. 4 (iZm005854-01), SEQUENCE ID NO. 5 (iZm010719-01), and SEQUENCE ID NO. 6 (iZm007840-01).

The present invention further comprises a vector (e.g., a recombinant DNA vector) comprising an expression cassette of this invention.

Further provided herein is a transgenic plant cell comprising an expression cassette of this invention, as well as a transgenic plant or progeny thereof comprising the transgenic plant cell of this invention.

In some aspects, the transgenic plant or progeny thereof can be a monocot plant. In some aspects, the transgenic plant or progeny thereof of this invention can be a dicot plant. Nonlimiting examples of a plant of this invention include maize, rice, soybean, sunflower, wheat, tomato, potato, sugarcane, barley, sugarbeet and tobacco.

The present invention also provides seed from the transgenic plant or progeny thereof of this invention.

In yet further aspects, the present invention provides a method of producing a protein in a plant cell comprising introducing an expression cassette and/or vector of this invention into the plant cell under conditions whereby the nucleic acid molecule of interest is expressed to produce the protein, thereby producing the protein in a plant cell.

Also provided herein is a method of producing a transgenic plant, comprising: a) introducing the expression cassette of any of claims 1 and 2 or the vector of claim 3 into a plant cell; and b) regenerating a plant or progeny thereof from the plant cell.

The present invention additionally provides a plant cell produced by the methods of this invention, as well as a plant or progeny thereof produced by the methods of this invention.

As also used herein an intron that is a non-heterologous intron or that is an intron that is not heterologous to a promoter to which the intron is operably linked in an expression cassette is an intron increases expression of the nucleotide sequence of interest.

As used herein, a terminator that is heterologous to a promoter in an expression cassette comprising the terminator and promoter describes a terminator that is increases expression of the nucleotide sequence of interest.

Recombinant DNA methods require the presence of specific restriction endonuclease sites at the termini of the DNA molecules to be joined. The most efficient practice requires the sites in one molecule to complement the sites in the other molecule. For example, a plasmid with SacI and NotI restriction endonuclease sites is required to ligate a nucleic acid molecule of interest (NOI) with SacI and Not I restriction endonuclease sites at its termini. Ideally, these sites are unique, that is they should not occur at any other place in either molecule. If these sites occur internally, they hinder manipulation by recombinant DNA methods and should be eliminated. Site-directed mutagenesis is one method of eliminating such sites. Techniques such as partial digestion followed by gel-purification of the appropriately sized fragment will also accomplish this without eliminating the internal restriction endonuclease sites, but are far less efficient and therefore less desirable.

The present invention recognizes that chemical synthesis, which is use of synthetic chemical technology as opposed to enzyme-mediated technology, of a polynucleotide molecule can replace or substitute for recombinant DNA methods in the construction of a polynucleotide molecule comprising a specific nucleotide sequence.

EXAMPLES

Example 1

This study sought to identify and test maize introns for expression cassette enhancement activity. This activity is best described as that which imparts improved protein production by an expression cassette when the intron is incorporated into that expression cassette This work queried the maize genome for each gene's first intron. Candidate introns were the n analyzed for free energy ($\Delta G$) score or IMEter score. The ViennaRNA package version 1.8.2 is used to calculate the free energy for each input sequence. (Hofacker et al. Monatshefte f. Chemie 125:167-188 (1994); tbi.univie.ac.at/RNA/). The parameter settings for calculation were "-p0-d2," which turns on calculation of the partition function and ensures that the partition function and the minimum free energy treat dangling end energies in the same manner. Calculation of the energies was executed on the in-house Linux cluster. In this manner, the free energy value and free energy per base pair were determined for each intron. The IMeter Score for each generated sequence is deter mined using the method of Rose et al. (Plant Cell 20:543-551 (2008)) as described herein. The free energy value can be the free energy or the mean free energy value. For example, an input intron nucleotide sequence is selected and using RNAfold, the free energy value for the intron nucleotide sequence is determined. These scores are thought to describe structural properties of the intron. A higher the IMEter score suggests the intron can improve the productivity of a transgene. This analysis sought to identify first introns predicted to improve transgene performance. The metric is protein production when the intron is present vs. protein production when the natural first intron is present. The iMEter score for the first introns known to be present in the maize genome was calculated and used to rank the introns. This was the first step.

The second step was to identify the subset of introns that belong to highly transcribed, constitutive genes. The results were used to identify introns for experimental analysis. The structure of the top-ranking candidate genes was examined to verify the gene model represented a bona fide gene. Table 1 lists the five maize introns that were selected for analysis. In add ition we examined the iUbi1-17 intron derived from the GRMZM2G409726 gene. These introns will be examined in the context of a weak promoter derived from the GRMZM2G002825 gene which is called ZmABP3 and a strong constitutive promoter derived from the GRMZM2G118637 gene which is called ZmUbi361. The $\Delta G$ calculated for the first introns of these genes are listed below.

iZmABP3-01=-408.11 kcal/mol (980 bp=-0.416 kcal/mol/bp)
iUbi1-17=-289.21 kcal/mol (1010 bp=-0.286 kcal/mol/bp)
iZmUbi361-01=190.46 kcal/mol (1329 bp=0.143 kcal/mol/bp)

In addition the influence of terminators on expression cassette activity was also examined. In this study tZmUbi158, tZmUbi361, tZmHSP70, tNOS and tUbi1 were used as heterologous terminators. The basis for this work was the ZmABP3 expression cassette which is active in all plant tissues but pollen. It produces less protein compared to strong, constitutive expression cassettes like ZmUbi1.

Example 2

Transient expression assays in Black Mexican Sweet (BMS) maize cells were primarily used to compare protein production of the various expression cassette constructs. A combination of recombinant DNA and DNA synthesis methods was used to construct each expression cassette which used the ClonTech AcGreen fluorescent protein as a reported. The focus was prZmABP3, in the "native gene" expression cassette context. In most expression cassettes only the intron is replaced, nothing else. This study examined the influence of introns listed in Table 1, the ZmUbi1 intron (iUbi1-17) and the eFMV/e35S transcriptional enhancer on behaviour of the ZmABP3 promoter (or expression cassette) in the BMS system.

Briefly, the cells were immobilized on filter paper and transformed with the expression cassette by particle bombardment. The filter paper was then placed on nutrient media and incubated for several hours. During the incubation period transfected cells were periodically scored for expression cassette activity by quantifying AcGreen fluorescence. To control for variability in BMS cell batches, all constructs were examined in the same study.

The time at which peak AcGreen fluorescence occurred was selected to compare expression cassette activity. The signal for the baseline expression cassette was set at 100 and the signals collected for the other expression cassettes in the study are reported relative to the baseline.

Data from the ZmABP3 intron study are shown in Table 2. The results show that replacement of iZmABP3 with iZm10430-01 produced a ~2× increase in expression activity. The difference between iZm10430-01 and iZm10430-02 is a single base change to remove an internal BamHI site. This change did not affect the intron's activity. The iZm10430 intron consistently increased ZmABP3 expression cassette activity, sometimes up to 10-fold. The iZm010719-01 intron slightly improved the ZmABP3 promoter (1.25×) and the remaining introns reduced activity by more than half. Overall two of the five identified introns in Table 1 improved ZmABP3 expression cassette activity.

We also examined replacement of iZmABP3 with iUbi1-17 which is derived from a gene with proven high, constitutive activity in transgenic maize. Table 2 shows the 15023AcGi19499 expression cassette showed a slight decrease in expression (0.7×) relative to the baseline expression cassette. The results suggest that simply relying on components derived from well-characterized trait gene expression cassettes is not sufficient to improve the activity of weak expression cassettes.

Trait gene expression cassettes, based on candidate plant genes, are often desirable because they have specific spatial and/or temporal activity profiles. The ZmABP3 expression cassette is active in all tissues but pollen (U.S. Pat. No. 8,344,209). This specificity is often accompanied by low protein production levels. One tool to improve protein production is the eFMV/e35S enhancer complex. Its activity on the baseline ZmABP3 expression cassette was examined in the BMS system. Results in Table 2 show that the eFMV/e35S enhancer complex increases expression cassette activity by 1.3 fold. In other studies activity improvement of up to 5-fold was observed. These results are consistent with eFMV/e35S enhancer complex induced activity improvement observed in stable transgenic maize (U.S. Pat. No. 8,344,209, Example 1.9) suggesting that the BMS cell system is an effective tool to evaluate the components being tested here.

Example 3

The ZmUbi361 expression cassette is derived from the GRMZM2G118637 gene which possesses an intron (iZmUbi361-01) with suboptimal ΔG properties. The theory outlined in Example 1 indicates that a more negative ΔG is better. In this study the effect of introns listed in Table 1 was examined in the context of the ZmUbi361 expression cassette which is considered a strong constitutive expression cassette when used in transgenic maize. As in Example 2, only iZmUbi361-01 was replaced, and no other sequence was altered during the construction of each expression cassette listed in Table 3.

Briefly, the cells were immobilized on filter paper and transformed with the expression cassette by particle bombardment. The filter paper was then placed on nutrient media and incubated for several hours. During the incubation period transfected cells were periodically scored for expression cassette activity by quantifying AcGreen fluorescence. To control for variability in BMS cell batches, all constructs were examined in the same study.

The time at which peak AcGreen fluorescence occurred was selected to compare expression cassette activity. The signal for the baseline expression cassette was set at 100 and the signals collected for the other expression cassettes in the study are reported relative to the baseline.

Results in Table 3 show that most of the introns improved ZmUbi361 expression cassette activity. The iZm10430-02 did the best, improving baseline expression cassette activity by 4.6 fold. The remaining introns improved baseline expression cassette activity by 1.25-2.15 fold. Only iZm005854-01 had no expression cassette improvement activity.

The effect of the tobacco mosaic virus Ω-translational enhancer (eTMV) was also evaluated in the context of the ZmUbi361 expression cassette using this system. Table 3 shows that construct 17627 produces activity that is roughly half the baseline activity. Previous work with eTMV in stable transgenic maize showed that this element tends to reduce overall transgene activity when used in transgenic maize. This provides further evidence that the BMS cell assay system used here reflects transgene activity in stable transgenic plants.

Overall the results in Table 3 show the effectiveness of the enhancing introns identified here. Only one intron did not possess enhancement activity.

Example 4

Examples 2 and 3 show that iZm10430 was capable of enhancing the activity of distinct expression cassettes using the BMS cell assay system. In this study iZm10430 was examined for expression cassette enhancement activities in stable transgenic maize. The OsMADS6 expression cassette, which has been shown to drive protein production in maize female reproductive tissue was used as the basis for this work. The expression cassettes were designed to produce two different versions of a rice trehalose-6-phosphate phosphatase (T6PP) protein.

The expression cassettes were constructed in a standard *Agrobacterium* binary vector. In the constructs containing the eFMV/e35S enhancer complex, the enhancer was placed immediately upstream of the OsMADS6 promoter. In the constructs containing the iZm10430 the intron in the promoter (iOsMADS6-01, 2757 bp) which is the first intron naturally found in the OsMADS6 gene was precisely replaced with iZm10430-01. The constructs were stably transformed into maize using standard procedures.

A qRT-PCR assay was used to assess the performance of each construct. The OsMADS6 expression cassette is known to produce transcript in leaf tissue of primary transformants, and qRT-PCR data are typically used to identify and rank transgenic events. Only data from single-copy, backbone-free events (N) are summarized in Table 4. The data in Table 4 show that the OsMADS6 expression cassette is typically not highly active in T0 maize leaf. Inclusion of the eFMV/e35S enhancer complex increases transcript abundance by 48 to 118 fold. Replacement of iOsMADS6-01 with iZm10430-01 increases transcript abundance by 3.9 to 8.6 fold. These results demonstrate that iZm10430-01 functions to improve the activity of an expression cassette based on a rice gene in transgenic maize.

Example 5

The ability of plant gene-based terminators to function with a heterologous promoter was also examined to determine if terminators derived from well-characterized constitutive genes could improve the performance of less active promoters. The ZmABP3 expression cassette produces a highly desirable activity pattern. It is moderately active in all tissues and inactive in pollen. Greater activity is required to make it useful for applications such as insect control gene expression. It's possible that use of a heterologous terminator to replace the ZmABP3 terminator might improve expression cassette activity.

The terminators from four highly transcribed maize genes and the *Agrobacterium* nopaline synthase (NOS) gene were identified as candidates. The Ubi1, ZmUbi158 and ZmUbi361 genes were introduced in previous examples. The ZmHSP70 expression cassette is based on the maize GRMZM2G340251 gene, which global gene expression data indicate is a highly active, constitutive maize gene. The tZmABP3-01 terminator in the ZmABP3 expression cassette was replaced with each of the above terminators. The terminators are flanked with SacI/XhoI restriction endonuclease sites making this a simple recombinant DNA procedure. Transient expression assays in Black Mexican Sweet (BMS) maize cells were used to compare protein production of the various expression cassette constructs.

Briefly, the BMS cells were immobilized on filter paper and transformed with the expression cassettes listed in Table 5 by particle bombardment. The filter paper was then placed on nutrient media and incubated for several hours. During the incubation period transfected cells were periodically scored for expression cassette activity by quantifying AcGreen fluorescence. To control for variability in BMS cell batches, all constructs were examined in the same study.

The time at which peak AcGreen fluorescence occurred was selected to compare expression cassette activity. The signal for the baseline expression cassette was set at 100 and the signals collected for the other expression cassettes in the study are reported relative to the baseline.

Data from the ZmABP3 terminator study are shown in Table 5. The data in Table 5 show that the terminator swaps improved protein production less than 2-fold (tZmUbi361 and tNOS) or improved protein production 2.5-4 fold (tUbi1, tZmUbi158 and tZmHSP70). In all cases the heterologous terminator improved expression cassette activity relative to the promoter's natural terminator. The CaMV35SAcG expression cassette is included as a positive control that's known to deliver very high transgene expression in stably transformed maize. Only the tZmUbi158 substituted expression cassette comes close to the activity produced by this control. The results suggest that terminator substitution may make the ZmABP3 promoter as active as some of the more effective constitutive promoters.

Although the foregoing invention has been described in some detail by way of illustration and example for purposes of clarity of understanding, it will be obvious that certain changes and modifications may be practiced with the scope of the present invention.

TABLE 1

Maize introns identified to enhance expression cassette productivity

| Probe | Intron Name | Gene Model | CDS (4a.53) | ΔG | Imeter score | Intron Length (bp) | Imeter/ length | SEQ ID NO: |
|---|---|---|---|---|---|---|---|---|
| Zm008975_at | iZm008975-01 | GRMZM2G061447 | GRMZM2G061447_T03 | −605.5 | 587.7 | 1648 | 0.3566 | 1 |
| Zm005854_s_at | iZm005854-01 | GRMZM2G019200 | GRMZM2G019200_T03 | −728.8 | 448.5 | 1969 | 0.2278 | 2 |
| Zm010430_at | iZm10430-01 &-02 | GRMZM2G164265 | GRMZM2G164265_T04 | −273.9 | 427.8 | 696 | 0.6146 | 3 |
| Zm010719_at | iZm010719-01 | GRMZM2G098237 | GRMZM2G098237_T01 | −328 | 330.3 | 792 | 0.4171 | 4 |
| Zm007840_at | iZm007840-01 | GRMZM2G132854 | GRMZM2G132854_T01 | −231.8 | 291.7 | 602 | 0.4845 | 5 |

TABLE 2

Transient expression level of ZmABP3 intron swap constructs in BMS cells.

| Expression cassette | Type of swap | Promoter | Intron | Terminator | Expression level relative to baseline (%) |
|---|---|---|---|---|---|
| 15023AcGreen | baseline | prZmABP3-01 | iZmABP3-01 | tZmABP3-01 | 100 |
| 15023AcGi19491 | intron | prZmABP3-01 | iZm10430-01 | tZmABP3-01 | 175 |
| 15023AcGi20754 | intron | prZmABP3-01 | iZm10430-02 | tZmABP3-01 | 225 |
| 15023AcGi20755 | intron | prZmABP3-01 | iZm010719-01 | tZmABP3-01 | 125 |
| 15023AcGi20751 | intron | prZmABP3-01 | iZm005854-01 | tZmABP3-01 | 30 |
| 15023AcGi20752 | intron | prZmABP3-01 | iZm007840-01 | tZmABP3-01 | 30 |
| 15023AcGi20753 | intron | prZmABP3-01 | iZm008975-01 | tZmABP3-01 | 30 |
| 15023AcGi19499 | intron | prZmABP3-01 | iUbi-17 | tZmABP3-01 | 70 |
| 15023AcGeFMVe35S | eFMV-e35S enhancer | prZmABP3-01 | iZmABP3-01 | tZmABP3-01 | 130 |
| CaMV35SAcG | positive check | CaMV35S | | tNOS | 160 |

TABLE 3

Transient expression level of ZmUbi361 component swap constructs in BMS cells.

| Expression cassette | Type of swap | Enhancer | Promoter | Intron | Terminator | Expression level relative to baseline (%) |
|---|---|---|---|---|---|---|
| 19404 | baseline | | prZmUbi361-02 | iZmUbi361-01 | tZmUbi361-01 | 100 |
| 20749 | intron | | prZmUbi361-02 | iZm10430-02 | tZmUbi361-01 | 460 |
| 20748 | intron | | prZmUbi361-02 | iZm008975-01 | tZmUbi361-01 | 215 |
| 20747 | intron | | prZmUbi361-02 | iZm007840-01 | tZmUbi361-01 | 160 |
| 20750 | intron | | prZmUbi361-02 | iZm010719-01 | tZmUbi361-01 | 125 |
| 20746 | intron | | prZmUbi361-02 | iZm005854-01 | tZmUbi361-01 | 100 |
| 17267 | intron | eTMV | prZmUbi361-02 | iZmUbi361-01 | tZmUbi361-01 | 55 |
| CaMV35SAcG | positive check | | CaMV35S | | tNOS | 25 |

TABLE 4

Summary of OsMADS6 expression cassette data in stable transgenic maize

| Construct | Trait | Enhancer | Tissue | qRT-PCR (mean) | qRT-PCR- (StDev) | N |
|---|---|---|---|---|---|---|
| 20832 | OsMADS6-T6PP-8H | none | leaf | 80.08 | 165.54 | 26 |
| 20833 | en-OsMADS6-T6PP-8H | eFMV/e35S | leaf | 3878.05 | 1409.21 | 23 |
| 20848 | OsMADS6(Δi)-T6PP-8H | iZm10430-01 | leaf | 315.96 | 164.04 | 8 |
| 20571 | OsMADS6-T6PP-9Y | none | leaf | 52.31 | 49.50 | 30 |
| 20569 | en-OsMADS6-T6PP-9Y | eFMV/e35S | leaf | 6153.63 | 5510.96 | 85 |
| 20640 | OsMADS6(Δi)-T6PP-9Y | iZm10430-01 | leaf | 451.56 | 284.63 | 30 |

The qRT-PCR data are reported in relative units. Data are the mean ± standard deviation of four assays.

TABLE 5

Transient expression level of ZmABP3 terminator swap constructs in BMS cells.

| Expression cassette | Type of swap | Promoter | Intron | Terminator | Expression level relative to baseline (percent) |
|---|---|---|---|---|---|
| 15023AcGreen | baseline | prZmABP3-01 | iZmABP3-01 | tZmABP3-01 | 100 |
| 15023AcGtHSP | terminator | prZmABP3-01 | iZmABP3-01 | tZmHSP70-01 | 380 |
| 15023AcGt158 | terminator | prZmABP3-01 | iZmABP3-01 | tZmUbi158-01 | 400 |
| 15023AcGtUbi | terminator | prZmABP3-01 | iZmABP3-01 | tZmUbi1-01 | 250 |
| 15023AcGt361 | terminator | prZmABP3-01 | iZmABP3-01 | tZmUbi361-01 | 140 |
| 15023AcGtNOS | terminator | prZmABP3-01 | iZmABP3-01 | tNOS-05-01 | 180 |
| CaMV35SAcG | positive check | CaMV35S | | tNOS | 420 |

What is claimed is:

1. An expression cassette comprising a promoter operably linked to a nucleic acid molecule of interest, which is operably linked to a terminator, further comprising a heterologous intron that enhances expression of the nucleic acid molecule of interest,
    wherein the heterologous intron is heterologous to at least one of the nucleic acid molecule of interest, the promoter, and the terminator, and
    wherein the heterologous intron is selected from the group consisting of SEQ ID NO: 1 and SEQ ID NO: 2.

2. The expression cassette of claim 1 wherein the promoter and terminator originate from a common gene locus.

3. A recombinant vector comprising the expression cassette of claim 1.

4. A transgenic plant cell comprising the expression cassette of claim 1.

5. A transgenic plant or progeny thereof comprising the transgenic plant cell of claim 4.

6. A transgenic plant according to claim 5, wherein said plant is a monocot plant.

7. A transgenic plant according to claim 6, wherein said plant is a maize plant.

8. Seed from the transgenic plant of claim 7, wherein the seed comprises the expression cassette.

9. A method of producing a protein in a plant cell, the method comprising introducing the expression cassette of claim 1 into the plant cell under conditions whereby the nucleic acid molecule of interest is expressed to produce a protein.

* * * * *